United States Patent [19]

Tu

[11] Patent Number: 4,764,167

[45] Date of Patent: Aug. 16, 1988

[54] SAFETY NEWBORN MUCOUS SUCTION DEVICE

[76] Inventor: Ho C. Tu, 241 NE. 199th La., North Miami Beach, Fla. 33179

[21] Appl. No.: 140,970

[22] Filed: Jan. 7, 1988

Related U.S. Application Data

[63] Continuation-in-part of Ser. No. 3,269, Jan. 14, 1987, abandoned.

[51] Int. Cl.$^4$ ............................................. A61M 25/00
[52] U.S. Cl. ........................................ 604/73; 604/320
[58] Field of Search ................................... 604/73–76, 604/119, 280–283, 320; 128/207.14, 207.15

[56] References Cited

U.S. PATENT DOCUMENTS

| | | | |
|---|---|---|---|
| 2,628,615 | 2/1953 | Saffin | 604/148 |
| 3,050,062 | 8/1962 | Ulmer | 604/76 X |
| 3,612,089 | 10/1971 | Beguiristain | 604/320 X |
| 3,811,485 | 5/1974 | Holbrook | 604/320 X |
| 4,275,724 | 6/1981 | Behrstock | 604/164 X |
| 4,662,367 | 5/1987 | Gore | 604/73 X |

Primary Examiner—Dalton L. Truluck
Attorney, Agent, or Firm—Alvin S. Blum

[57] ABSTRACT

A suction apparatus for aspirating mucous from the nose, mouth and throat of the newborn to clear the respiratory passages after birth. Includes a catheter with a tip sized and shaped for the newborn, a mucous trap to collect the aspirated mucous, and a suction tube and mouthpiece to permit the application of controlled suction by the attending physician. The device incorporates safety features to prevent the accidental ingestion of dangerous microorganisms along with the aspirated air. These safety features include devices to close off the suction tube when mucous is about to enter it and filters to strain out any potential aerosols of mucous from the air entering the mouthpiece.

21 Claims, 2 Drawing Sheets

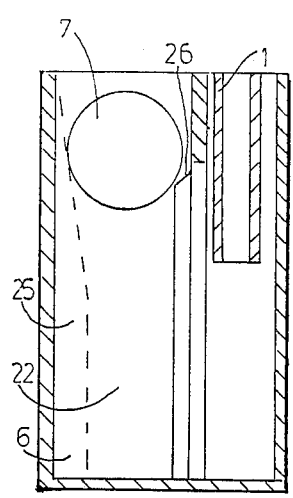
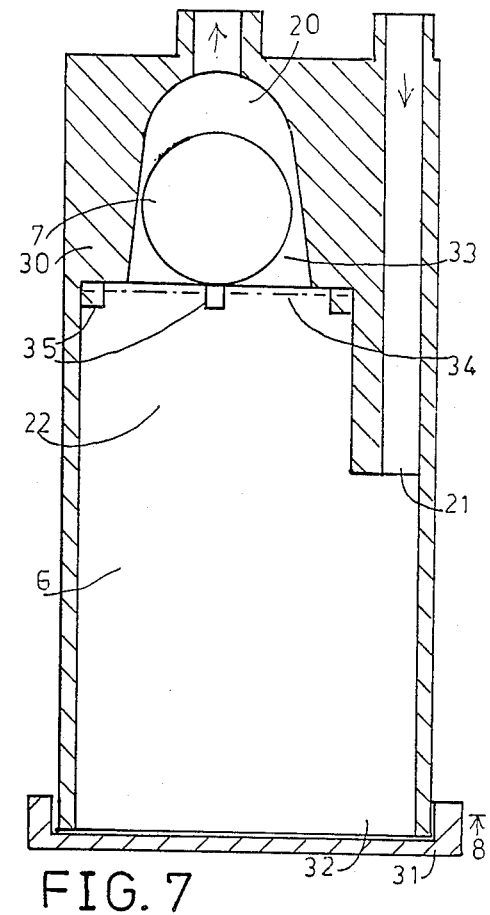
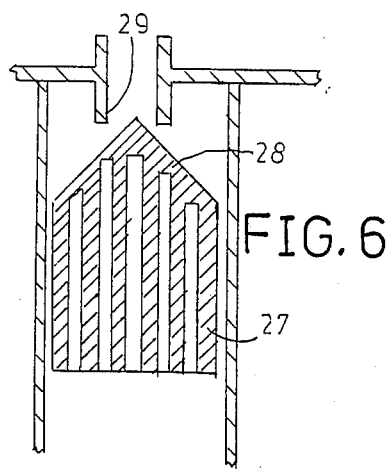
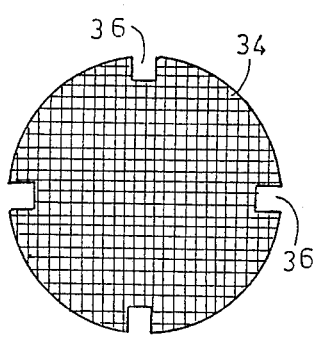
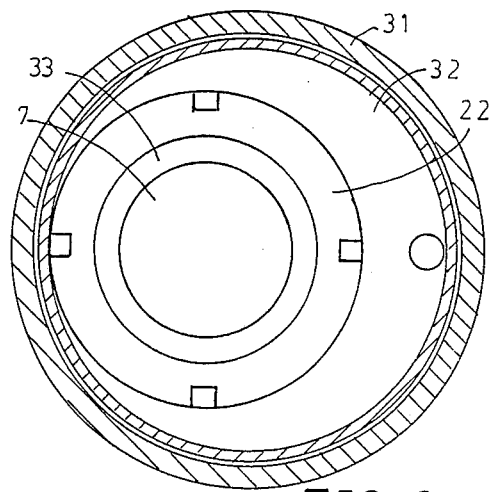
FIG.5
FIG.6
FIG.7
FIG.9
FIG.8

SAFETY NEWBORN MUCOUS SUCTION DEVICE

This is a continuation-in-part of Ser. No. 07/003,629 filed 1/14/87, now abandoned.

This invention relates to devices for aspirating mucous from the upper respiratory passages of newborns at birth, and more particularly to such devices incorporating safety features to prevent the ingestion of harmful microorganisms during the application of mouth suction by the user.

BACKGROUND OF THE INVENTION

It is common practice to remove mucous from the nasal passages, mouth and throat of a newborn baby to clear the upper respiratory passages for respiration and to prevent the unfavorable effects of that mucous being drawn into the lungs of the newborn. It has been found that the mucous can be cleared most effectively by suction through a catheter, with suction provided by the attending physician or nurse through a mouthpiece via a flexible suction tube. As shown in FIG. 1, which illustrates the apparatus of the prior art, the baby catheter 1, and the mouthpiece 2 and suction tube 5 meet at a mucous trap 6. The portion of the suction tube within the trap is short and the portion of the catheter tube within the trap is longer. This ensures that the user will aspirate air and the mucous will be trapped in trap 6. However, if the trap fills with mucous and bubbles of mucous, some may be drawn into the mouth of the user.

Because the mucous coming from the lungs generally contains a special surfactant (reduced in the respiratory distress syndrome) that encourage foaming, the mucous will foam and bubble if air is aspirated along with the mucous. The operator will ordinarily aspirate some air, as this is his indication that all the mucous has been aspirated. Some of these newbors may be infected with certain dangerous microorganisms such as AIDS, Herpes, Gonnorhea, Syphillis, etc. that represent a threat to the health of the user. Because this threat to the user is increasing, some hospitals are prohibiting the use of this device and require the use of a suction machine which is more awkward to use and presents more risk to the baby because suction is more difficult to control. Furthermore, these suction machines may spray an aerosol of mucous into the room if not carefully operated or controlled, thereby increasing the hazard they intended to avoid.

SUMMARY OF THE INVENTION

It is an object of the invention to provide a suction device for aspirating mucous from the nose, mouth and throat of a newborn baby using mouth suction that traps the mucous and prevents the accidental aspiration by the user of that mucous or any portion thereof in the form of liquid, foam, bubbles, and droplets from breaking bubbles and the like. The device includes a long flexible catheter tube with a tip of a size and shape to fit the passages to be cleared of mucous. The other end of the catheter terminates within a trap chamber. A long, flexible suction tube has a mouthpiece at a first end to fit the mouth of the user. The suction tube terminates at a second end within the trap chamber at a sealing seat. The trap chamber is hermetically sealed with the catheter and suction tube entering at the top so that when the user applies mouth suction to the mouthpiece, suction is transmitted through the trap to the catheter tip. When mucous is drawn into the catheter, it is deposited in the trap. A lightweight, floating sealing member is contained within the trap. As the trap fills with mucous, the sealing member floats atop the mucous. The floating member and the sealing seat at the terminus of the suction tube within the trap are so arranged that the floating member fits into the sealing seat and closes off the suction tube before the mucous reaches the suction tube, thereby preventing the aspiration of mucous by the user. Also included are filter means to filter out any potential aerosols of mucous that may be generated by bursting bubbles from the air entering the mouthpiece. The combination ensures that the more convenient and controllable mouth suction may be employed with safety to both the patient and the user.

Additional objects, features and advantages of the invention will be understood from the following description and accompanying drawings.

BRIEF DESCRIPTION OF THE DRAWINGS

FIG. 5 is a front elevation, in cross section, of the chamber of FIG. 2 with alternate sphere retainers.

FIG. 6 shows, in cross section, a front elevation of a detail of a conical floating member.

FIG. 7 is a front elevation, in cross section, of an embodiment of the invention joined at the bottom.

FIG. 8 is a cross section through plane 8—8 of FIG. 7.

FIG. 9 is a top plan view of the retaining screen of FIG. 7.

DETAILED DESCRIPTION OF PREFERRED EMBODIMENTS

Figure 1:
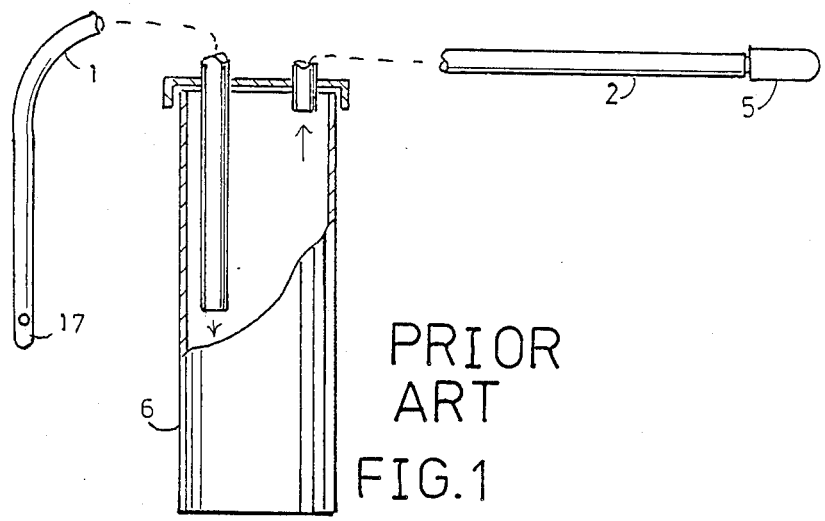
FIG. 1 is a front elevation of a device of the prior art.
Figure 2:
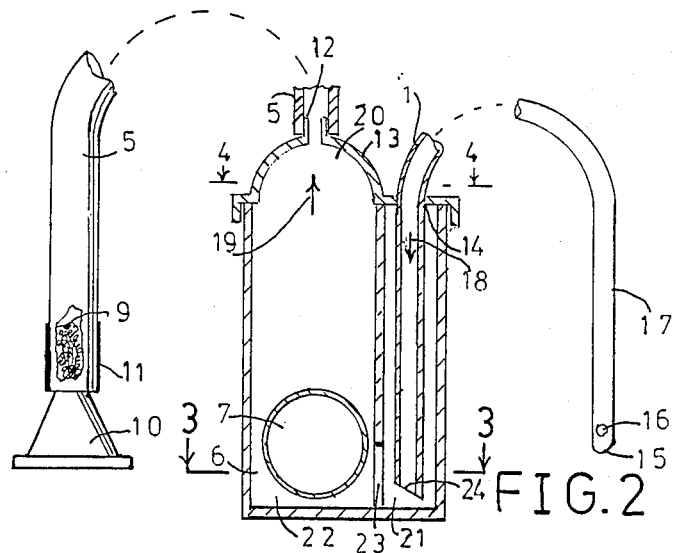
FIG. 2 is a front elevation, in cross section, of an embodiment of the invention joined at the top.
Figure 3:
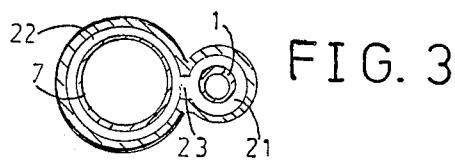
FIG. 3 is a cross section through plane 3—3 of FIG. 2.
Figure 4:
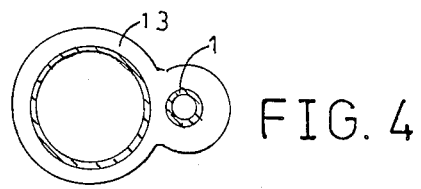
FIG. 4 is a cross section through plane 4—4 of FIG. 2.

Referring first to FIG. 2,3 and 4 a mouthpiece 10 is sealed in one foot long flexible suction tube 5. A filter exemplified by a cotton plug 9 in a dilated section 11 of suction tube 5 filters out any fine mist generated by bubbles of mucous. Tube 5 is sealed to tubulation 12 of molded top member 13. Top member 13 also has an aperture 14 through which is extended the catheter 1. Catheter 1 is resilient and is molded with a constriction at the aperture to make a fixed hermetic seal by means well known in the art. The catheter 1 terminates in a small diameter tip 17 with an end aperture 15 and a side aperture 16.

A bottom chamber 6 traps the mucous that enters (arrow 18) through catheter 1 when suction is applied (arrow 19) to suction tube 5. The top member 13 is molded to hermetically seal onto the chamber 6 so that the suction applied to the mouthpiece 10 is transmitted to the catheter tip 17 and results in the transfer of mucous from the patient into chamber 6. To prevent the transfer of mucous to the mouth of the user, the suction tube 5 does not extend into the chamber 6. Furthermore, the hemispherical cavity 20 molded into top member 13 acts as the seat of a check valve arrangement to prevent the passage of mucous into the suction tube 5. A very light, thin-walled, spherical float 7 floats on top of the mucous as it accumulates in chamber 6 and the float enters into the cavity 20 and seals off the suction tube before mucous can enter tube 5. The chamber 6 includes two cylindrical chambers, a smaller chamber 21 that contains the catheter 1 and a larger chamber 22 that contains the float 7. The cylinders are parallel and juxtaposed and communicate along a portion of their length through passage 23. Cylinder 22 guides float 7 into hemispherical cavity 20 as the level of trapped mucous rises to ensure that the float 7 will seat in the cavity 20 and seal off the suction tube and prevent the potentially harmful ingestion of mucous by the user. The float 7 may be of thin-walled, hollow construction. Alternatively, it may be constructed of a closed-cell foam or other very light weight material. The catheter 1, at its termination inside the chamber is shown with a diagonal end 24 to ensure that it will not be inadvertently sealed against the bottom if chamber 6 is inserted too far. As shown in FIG. 5, the catheter 1 may alternatively extend only part way down into chamber 6. This requires fixing catheter 1 into the top member, but is has the advantage of reducing foam formation when air is inadvertently aspirated. FIG. 5 further illustrates alternative embodiments of the chamber 6, wherein the float 7 is releasably held by gravity near its seated position so that it need not travel very far to seal off the suction tube. The float-containing cylinder 22 may be slightly tapered (phantom line 25) to prevent float 7 from falling to the bottom. Alternatively, several vertical ribs 26 may prevent float 7 from falling to the bottom. FIG. 6 shows an alternative check-valve arrangement, wherein a floating cylinder 27 has a conical top 28. Alternatively, the top may have a hemispherical shape. The seat for the valve is a downward-directed tube 29. FIGS. 7,8 show another embodiment wherein the cylinder and upper seal and connections are molded in one top piece 30 and a circular disc cap 31 is sealed to the bottom to form the chamber 6. The molded top piece 30 includes a large lower cylindrical chamber 32 communicating at its upper end with the two cylindrical chambers 21 and 22 for the catheter inlet and the float respectively. The float 7 is held in a tapered cylinder 33 by a retaining screen 34 (FIG. 9). The retaining screen 34 is held in place by a jam fit on retaining lugs 35 molded into top 30. The lugs 35 fit into slightly smaller notches 36 cut in screen 34. The screen 34 also helps to stop bubbles as does the narrow space between float 7 and cylinder 33. Fluid flow to the lower extremity 29 (FIG. 6) of the vacuum port must pass through this narrow space between buoyant float and the float valve housing cylinder which, as shown, is open only at its lower end. This narrow space will prevent the passage of foam and act as a baffle in cooperation with the space above the float to inhibit the passage of droplets. The check valve action of float 7 in seat 20 in sealing off the suction tube is as previously described.

The above disclosed invention has a number of particular features which should preferably be employed in combination although each is useful separately without departure from the scope of the invention. While I have shown and described the preferred embodiments of my invention, it will be understood that the invention may be embodied otherwise than as herein specifically illustrated or described, and that certain changes in the form and arrangement of parts and the specific manner of practicing the invention may be made within the underlying idea or principles of the invention within the scope of the appended claims.

I claim:

1. A safety suction device for catheter aspiration of mucous from the nose, mouth and throat of a newborn by suction applied by the mouth of the user, comprising:

a. mucous collecting chamber means for trapping said mucous in the form of liquid, foam, bubbles and droplets as it is removed from said newborn;
   b. catheter means providing a conduit therethrough and having a first end constructed for insertion into the nose and mouth of said newborn and a second end connected to said chamber means, said conduit being in communication with said chamber means to transmit said suction from said chamber to said first end and to transmit said mucous from said first end into said chamber means under the force of said suction while preventing disease contamination of said user from said mucous;
   c. suction tube means providing a channel therethrough and having a first end terminating in mouthpiece means for insertion into the mouth of said user for the application of said suction and having a second end connected to and in channel communication with said chamber means at a vacuum port having a lower extremity to transmit said suction from said user to said chamber means for aspirating mucous through said catheter means; and
   d. check valve means in said chamber means for closing off said channel of said suction tube means when the level of said mucous collected in said chamber means reaches a predetermined level at which there is a danger of said mucous entering said mouth of said user said check valve means including a bouyant valve member, and a unitary valve housing sealably connected to said lower extremity and open only at its lower end, said housing thereby forming a substantially vertical channel for free vertical movement of said valve member and restraining lateral movement of said valve member, said check valve means providing a fluid-tight chamber above said valve member with the sole passage for fluid therethrough limited to exit at said lower extremity and entrance at a narrow perimeter space between said valve member and the interior walls of said channel to inhibit the passage of fluid in liquid, foam, bubble and droplet form to said mouth.

2. In the device of claim 1, said check valve means including a spherical float for floating atop said mucous in said chamber means.

3. In the device of claim 2, said float constructed of a closed cell foam.

4. In the device of claim 2, said float is a hollow sphere.

5. In the device of claim 2, said chamber means includes a lower, guide portion and a hemispherical portion above said guide portion, said guide portion providing a passage for guiding said float into said hemispherical upper portion as said level of mucous rises and said float floats atop said mucous, said hemispherical portion in communication with said suction tube means and also forming a valve seat into which said sphere seals to provide check valve operation and thereby prevent said mucous from entering said suction tube means.

6. In the device of claim 1, said check valve means includes a cylindrical float with a hemispherical top.

7. In the device of claim 6, said float is hollow.

8. In the device of claim 6, said float is constructed of closed cell foam.

9. In the device of claim 6, said float is constructed with a plurality of blind cylindrical channels for economy of manufacture and to reduce weight for better floating.

10. In the device of claim 6, said chamber means includes a lower guide portion and a hemispherical portion above said guide portion, said guide portion providing a passage for guiding said float into said hemispherical portion as said level of mucous rises and sid float floats atop said mucous, said hemisphere portion communicating with said suction tube means and also forming a valve seat into which said hemispherical top seals to provide check valve operation and thereby prevent said mucous from entering said suction tube means.

11. The device of claim 1, including filter means in said suction tube means to filter out mucous aerosols.

12. The device of claim 5, including float retaining means in said guide portion for holding said float in the upper portion of said chamber means close to said hemispherical upper portion to reduce the distance said float must travel to perform said check valve operation.

13. In the device of claim 12, said float retaining means including screen means.

14. In the device of claim 1, said float comprises a substantially cylindrical lower portion with a substantially conical top.

15. In the device of claim 14, said chamber means includes a lower guide portion and an upper portion with a downwardly projecting, substantially cylindrical tubular seating means in communication with said suction tube means, said guide portion providing a passage for said float to guide said conical top of said float into seating engagement with said tubular seating means as said level of mucous rises and said float floats atop said mucous to thereby prevent mucous from entering said suction tube means.

16. In the device of claim 2, said chamber means including a lower guide potion and an upper portion with a downwardly projecting, substantially cylindrical, tubular seating means in communication with said suction tube means, said guide portion providing a passage for said float to guide said float into seating engagement with said tubular seating means as said level of mucous rises and said float floats atop said mucous to thereby prevent said mucous from entering said suction tube means.

17. In the device of claim 16, said check valve means includes a cylindrical float with a hemispherical top.

18. The device of claim 16, including float retaining means in said guide portion for holding said float in the upper portion of said chamber means close to said seating means to reduce the distance said float must travel to perform said check valve operation.

19. In the device of claim 18, said float retaining means including screen means.

20. The device of claim 15, including float retaining means in said guide portion for holding said float in the upper portion of said chamber means close to said seating means to reduce the distance said float must travel to perform said check valve operation.

21. In the device of claim 20, said float retaining means including screen means.

* * * * *